(12) United States Patent
Le-Khac et al.

(10) Patent No.: US 7,432,384 B2
(45) Date of Patent: Oct. 7, 2008

(54) DIRECT EPOXIDATION PROCESS

(75) Inventors: Bi Le-Khac, West Chester, PA (US); Roger A. Grey, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 238 days.

(21) Appl. No.: 11/257,955

(22) Filed: Oct. 25, 2005

(65) Prior Publication Data

US 2007/0093669 A1   Apr. 26, 2007

(51) Int. Cl.
*C07D 301/10* (2006.01)
*C07D 301/12* (2006.01)

(52) U.S. Cl. .................. 549/533; 502/66; 502/245; 502/402; 549/531

(58) Field of Classification Search .............. 549/532, 549/533; 502/66, 243, 245, 402
See application file for complete search history.

(56) References Cited

U.S. PATENT DOCUMENTS

| 3,351,635 | A | 11/1967 | Kollar | 260/348.5 |
|---|---|---|---|---|
| 4,367,342 | A | 1/1983 | Wulff et al. | 549/529 |
| 4,410,501 | A | 10/1983 | Taramasso et al. | 423/326 |
| 4,833,260 | A | 5/1989 | Neri et al. | 549/531 |
| 4,994,589 | A | 2/1991 | Notermann | 549/534 |
| 5,623,090 | A | 4/1997 | Haruta et al. | 568/360 |
| 5,780,657 | A | 7/1998 | Cooker et al. | 549/534 |
| 5,824,622 | A | 10/1998 | Harmer et al. | 502/407 |
| 5,856,534 | A | 1/1999 | Cooker et al. | 549/534 |
| 6,008,388 | A | 12/1999 | Dessau et al. | 549/531 |
| 6,156,245 | A | 12/2000 | Takebayashi et al. | 264/4.7 |
| 6,362,349 | B1 | 3/2002 | Kuperman et al. | 549/533 |
| 6,399,794 | B1 * | 6/2002 | Hancu | 549/533 |
| 6,498,259 | B1 | 12/2002 | Grey et al. | 549/533 |
| 6,646,142 | B1 | 11/2003 | Meima et al. | 549/536 |
| 6,958,405 | B2 | 10/2005 | Le-Khac et al. | 549/531 |

FOREIGN PATENT DOCUMENTS

| BE | 1001038 A7 | 6/1989 |
|---|---|---|
| EP | 0 345 856 | 12/1989 |
| EP | 0 498 166 | 8/1992 |
| JP | 4-352771 | 12/1992 |

OTHER PUBLICATIONS

Lattanzi et al., Org. Lett., 2002, 4(9), 1519-1521.*
Dechow, Frederick, Separation and Purification Techniques in Biotechnology, Noyes Publications, 1989.*
S. Kobayashi et al., *Chem. Commun.* (2003) 449.
R. Akiyama et al., *Angew. Chem. Int. Ed.* 40 (2001) 3469.
S. Kobayashi et al., *J. Am. Chem. Soc.* 120 (1998) 2985.
R. Szostak, "Non-aluminosilicate Molecular Sieves," in *Molecular Sieves: Principles of Synthesis and Identification* (1989) pp. 205-282.
G. Vayssilov, *Catal. Rev.—Sci. Eng.* 39(3) (1997) 209.
F. Helfferich, *Ion Exchange* Chapter 3, (1962) pp. 26-71.
R. Albright, "Basic Principles of Catalysis by Functionalized Porous Organic Polymers," in *Catalyst Supports and Supported Catalysts* (1987) A. Stiles, Ed., pp. 159-186.
M. Donbrow, "Microcapsules and Nanoparticles" in *Medicine and Pharmacy* pp. 1-14, CRC Press, 1991.
G. Beestman, "Microencapsulation of Solid Particles" in *Controlled-Release Delivery Systems for Pesticides* (1999) H. Scher, Ed., pp. 31-54.
C. Ramarao et al., *Chem. Commun.* (2002) 1132 & 1134.
J. Q. Yu et al., *Chem. Commun.* (2003) 678.
H. Kage et al., *Adv. Powder Technol.* 13 (2002) 265.

* cited by examiner

*Primary Examiner*—B. Dentz
*Assistant Examiner*—David E Gallis
(74) *Attorney, Agent, or Firm*—Yuanzhang Han

(57) ABSTRACT

A process is disclosed for the epoxidation of an olefin with hydrogen and oxygen in the presence of an oxidation catalyst comprising a transition metal zeolite and a polymer-encapsulated noble metal catalyst. The noble metal catalyst comprises a noble metal and an ion-exchange resin. The process using the polymer-encapsulated noble metal catalyst gives higher epoxide productivity than a process that uses a noble metal catalyst which is not encapsulated by a polymer.

20 Claims, No Drawings

DIRECT EPOXIDATION PROCESS

FIELD OF THE INVENTION

This invention relates to a process for producing an epoxide from hydrogen, oxygen, and an olefin.

BACKGROUND OF THE INVENTION

Many different methods for the preparation of epoxides have been developed. Commercially, propylene oxide is produced by the chlorohydrin process or hydroperoxidation (see, e.g., U.S. Pat. Nos. 3,351,635 and 4,367,342; EP 0 345 856). Unfortunately, both processes have disadvantages. The chlorohydrin process suffers from the production of a dilute salt stream. The hydroperoxidation process, in which propylene is oxidized with an organic hydroperoxide such as ethylbenzene hydroperoxide or tert-butyl hydroperoxide, produces organic co-products such as t-butyl alcohol or styrene, whose value must be captured in the market place. Ethylene oxide is commercially produced by the direct oxidation of ethylene with oxygen over a silver catalyst. Unfortunately, efforts to epoxidize higher olefins (olefins containing three or more carbons) such as propylene with oxygen in the presence of a silver catalyst have failed to produce a commercial process (see, e.g., U.S. Pat. Nos. 5,856,534, 5,780,657 and 4,994,589).

Recent efforts have focused on the direct epoxidation of higher olefins with oxygen and hydrogen. For example, the reaction may be performed in the presence of a catalyst comprising gold and a titanium-containing support (see, e.g., U.S. Pat. Nos. 5,623,090, 6,362,349, and 6,646,142), or a catalyst containing palladium on a titanium zeolite (see, e.g., JP 4-352771).

Mixed catalyst systems for olefin epoxidation with hydrogen and oxygen have also been disclosed. For example, Example 13 of JP 4-352771 describes the use of a mixture of titanosilicate and Pd-on-carbon for propylene epoxidation. U.S. Pat. No. 6,008,388 describes a catalyst comprising a noble metal and a titanium or vanadium zeolite, but additionally teaches that the Pd can be incorporated into a support before mixing with the zeolite. The catalyst supports disclosed include silica, alumina, and activated carbon. U.S. Pat. No. 6,498,259 discloses the epoxidation of an olefin with hydrogen and oxygen in a solvent containing a buffer in the presence of a catalyst mixture containing a titanium zeolite and a noble metal catalyst. It also discloses that organic polymer resins such as polystyrene, styrene-divinylbenzene copolymer, crosslinked polyethyleneimines, and polybenzimidazole may be used as supports for the noble metal catalyst.

Recently, a technique called "microencapsulation" was used to prepare catalysts with improved properties (see Chem. Commun. (2003) 449 and references cited therein; Angew. Chem., Int. Ed. 40 (2001) 3469; J. Am. Chem. Soc. 120 (1998) 2985; U.S. Appl. Pub. Nos. 2005/0201925, 2005/0202957, and 2005/0203304). EP 0 498 166 A1 discloses an alumina-supported Pd catalyst impregnated with 4-bromostyrene or styrene that is subsequently polymerized (see Example 7 and Comparative Example 8). The poly(4-bromostyrene)-coated catalyst is active in generating hydrogen peroxide from hydrogen and oxygen. U.S. Appl. Pub. No. 2004/0184983 describes a catalyst consisting of: (a) one or more metals of the platinum group as active components; (b) one or more polyolefins; and (c) a carrier. The polyolefin is dissolved in a solvent and the resulting solution is used to impregnate the carrier or the catalyst.

SUMMARY OF THE INVENTION

The invention is an epoxidation process comprising reacting an olefin, hydrogen, and oxygen in the presence of an oxidation catalyst comprising a transition metal zeolite, and a polymer-encapsulated noble metal catalyst. The noble metal catalyst comprises a noble metal and an ion-exchange resin. The process using the polymer-encapsulated noble metal catalyst gives higher epoxide productivity than a process that uses a noble metal catalyst which is not encapsulated by a polymer.

DETAILED DESCRIPTION OF THE INVENTION

The process of the invention employs an oxidation catalyst comprising a transition metal zeolite. Zeolites generally contain one or more of Si, Ge, Al, B, P, or the like, in addition to oxygen. A transition metal zeolite is a crystalline material having a porous molecular sieve structure and containing a transition metal (e.g., titanium zeolites, vanadium zeolites). A transition metal is an element in Groups 3-12 of the Periodic Table. The first row of these elements includes elements from Sc to Zn. Preferred transition metals are Ti, V, Mn, Fe, Co, Cr, Zr, Nb, Mo, and W. Particularly preferred are Ti, V, Mo, and W. Most preferred is Ti. The type of transition metal zeolite employed depends upon a number of factors, including the size and shape of the olefin to be epoxidized. For example, it is preferred to use a relatively small pore zeolite such as a transition metal silicalite if the olefin is a lower aliphatic olefin such as ethylene, propylene, or 1-butene. Where the olefin is propylene, the use of a TS-1 (titanium silicalite-1, a titanium silicalite having an MFI topology analogous to that of the ZSM-5 aluminosilicate) is especially advantageous. For a bulky olefin such as cyclohexene, larger pore zeolites may be preferred.

Preferred titanium zeolites used in the oxidation catalyst include titanium silicates (titanosilicates). Preferably, they contain no element other than titanium, silicon, and oxygen in the lattice framework (see R. Szostak, "Non-aluminosilicate Molecular Sieves," in *Molecular Sieves: Principles of Synthesis and Identification* (1989), Van Nostrand Reinhold, pp. 205-282). Small amounts of impurities, e.g., boron, iron, aluminum, phosphorous, copper, and the like, and mixtures thereof, may be present in the lattice. The amount of impurities is preferably less than 0.5 weight percent (wt. %), more preferably less than 0.1 wt. %. Preferred titanium silicates will generally have a composition corresponding to the following empirical formula: $xTiO_2 \cdot (1-x)SiO_2$, where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable. Particularly preferred titanium zeolites include the class of molecular sieves commonly known as titanium silicalites (see *Catal. Rev.-Sci. Eng.*, 39(3) (1997) 209). Examples of these include TS-1, TS-2 (having an MEL topology analogous to that of the ZSM-11 aluminosilicate), and TS-3 (as described in Belgian Pat. No. 1,001,038). Titanium zeolites having framework structures isomorphous to zeolite beta, mordenite, and ZSM-12 are also suitable for use.

The oxidation catalyst may be a powder or it may be formed into particles of various shapes and sizes. Suitable oxidation catalysts have a particle size in the range of about 0.0001 to about 3 mm. A formed oxidation catalyst may be made by pelletization, spray-drying, extrudation, or the like.

It may contain other components such as silica, alumina, and titania, and the like, and mixtures thereof (e.g., as binder).

The oxidation catalyst may be encapsulated within a polymer. Suitable polymers and the methods of encapsulation described below for the encapsulation of the noble metal catalyst may be applied.

A polymer-encapsulated noble metal catalyst is employed in the process. The noble metal catalyst of the present invention comprises a noble metal. Suitable noble metals include gold, silver, platinum, palladium, iridium, ruthenium, osmium, and mixtures thereof. Preferred noble metals are Pd, Pt, Au, Re, Ag, and mixtures thereof. While any of the noble metals can be utilized, either alone or in combination, palladium and gold are particularly desirable. Typically, the amount of noble metal present in the catalyst will be in the range of from 0.01 to 20 wt. %, preferably 0.1 to 5 wt. %. The manner in which the noble metal is incorporated into the catalyst is not critical. For example, the noble metal may be supported on the ion-exchange resin by impregnation, ion exchange, adsorption, precipitation, or the like.

There are no particular restrictions regarding the choice of the noble metal compound or complex used as the source of the noble metal in the catalyst. Suitable compounds include nitrates, sulfates, halides (e.g., chlorides, bromides), carboxylates (e.g., acetate), and amine or phosphine complexes of noble metals (e.g., palladium(II) tetraammine bromide, tetrakis(triphenylphosphine) palladium(0)).

Similarly, the oxidation state of the noble metal is not critical. Palladium, for instance, may be in an oxidation state anywhere from 0 to +4 or any combination of such oxidation states. To achieve the desired oxidation state or combination of oxidation states, the noble metal compound after being introduced into the catalyst may be fully or partially pre-reduced. Satisfactory catalytic performance can, however, be attained without any pre-reduction.

The noble metal catalyst comprises an ion-exchange resin as a support. Ion-exchange resins are synthetic organic polymers having ion-exchange properties. Examples of ion-exchange resins can be found in *Ion Exchange*, Friedrich Helfferich, McGraw-Hill Book Company, Inc. (1962), pp. 26-71. Preferably the ion-exchange resin is crosslinked. Ion-exchange resins are categorized according to functionality as either strong or weak acids or bases. Acidic resins (cationic resins) generally contain sulfonic acid or carboxylic acid groups. Basic resins (anionic resins) generally contain amine, substituted amine, ammonium, or substituted ammonium groups. Particularly preferred resins include the addition copolymers prepared from vinyl monomers.

Although gelular ion-exchange resins can be used, macroreticular ion-exchange resins are preferred (see F. Helfferich, supra. pp. 59-60). Macroreticular resins consist of agglomerates of very small gelular microspheres. They have both micropores and macropores. The average pore diameter of the resin is preferably greater than 10 angstroms (Å), more preferably greater than 20 Å. The internal surface area of the resin is typically in the range of 1-1000 square meters per gram ($m^2/g$), preferably in the range of 10-900 $m^2/g$, more preferably in the range of 30-600 $m^2/g$ (see R. L. Albright, "Basic Principles of Catalysis by Functionalized Porous Organic Polymers," *Catalyst Supports and Supported Catalysts* (1987) A. B. Stiles, Ed., Butterworths Publishers, pp. 159-186).

Preferably, an acidic resin (cationic resin) is used. Particularly preferred resins are sulfonic acid polystyrene resins, i.e., crosslinked polystyrene containing sulfonic acid functional groups. Divinylbenzene is commonly used as the crosslinking agent. When an acidic ion-exchange resin is used, its protons may be partially or completely exchanged by other cations. The extent of exchange may be anywhere in the range of 0-100 mol. %. Preferably at least 1 mol. % of protons are exchanged by other cations; the resulting resin is referred to as a "cation-exchanged" resin. Suitable cations include alkali metal, alkaline earth metal, lanthanide metal, zinc, cadmium, ammonium, alkylammonium, alkylphosphonium ions, and the like, and mixtures thereof. Preferred cations include alkali metal and alkaline earth metal ions, and mixtures thereof. Particularly preferred cations include sodium, potassium, calcium, and magnesium ions, and mixtures thereof.

The capacity of the ion-exchange resin is not critical. The capacity is a measure of the concentration of the functional groups (e.g., sulfonic acid or carboxylic acid, amine, ammonium, substituted ammonium) in the resin. Suitable ion-exchange resins may contain 0.01-20 equivalents per kilogram (eq/kg) of functional groups. Preferred resins contain 0.1-15 eq/kg; particularly preferred resins contain 1-10 eq/kg. For example, Amberlyst 36 (an acidic resin available from Rohm & Haas) contains 5.4 eq/kg of sulfonic acid groups.

The noble metal catalyst may contain other components, e.g., titania, zirconia, niobia, silica, alumina, silica-alumina, titania-silica, zirconia-silica, niobia-silica, and the like, and mixtures thereof. A composite of an ion-exchange resin and any of the above components may also be used as a support for the catalyst. For instance, U.S. Pat. No. 5,824,622 discloses porous microcomposites comprising a perfluorinated ion-exchange polymer containing pendant sulfonic and/or carboxylic acid groups entrapped within and highly dispersed throughout a network of metal oxide. Similar microcomposites can be used in the present invention.

A polymer-encapsulated noble metal catalyst is used in the present invention. By "encapsulated," we mean that the catalyst is contained within and is surrounded by a layer of polymer. Because ion-exchange resins are typically supplied as beads of various sizes (e.g., from about 10 μm to about 2 mm), the noble metal catalyst comprising a transition metal and an ion-exchange resin typically have similar particle sizes as the ion-exchange resin used. Thus the polymer-encapsulation involves entrapping the noble metal catalyst within a polymeric coating.

Polymers suitable for use in making polymer-encapsulated noble metal catalysts include natural or synthetic organic polymers (containing carbon atoms) made by addition or condensation polymerizations. Generally, the polymers are homopolymers or random and block copolymers produced by free-radical, ionic, coordination, or condensation polymerization of one or more polymerizable monomers. Examples include polystyrenics, polyolefins, polyethers, polyureas, polyacrylics, polyurethanes, polyesters, polyamides, polysiloxanes, polysaccharides, polypeptides, poly-nucleotides, and the like, and mixtures thereof. Preferred are polystyrenics, polyolefins, and mixtures thereof. Particularly preferred is polystyrene. The polymers can be generated by bulk, solution, suspension, or emulsion polymerizations. The polymers can be hydrocarbons, or they can incorporate functional groups such as halogens, hydroxyl, amine, phosphine, phosphine oxide, arsine, sulfur, sulfur oxides, alkoxy, silane, siloxy, carboxy, or the like.

The order in which the noble metal addition to the ion-exchange resin and the polymer-encapsulation are carried out is not critical, as long as both the ion-exchange resin and the noble metal are essentially enveloped within a thin layer of polymer. In one preferred example, a noble metal is added to an ion-exchange resin to form a noble metal catalyst prior to its encapsulation. In another example, an ion-exchange resin is encapsulated within a polymer to produce a polymer-encapsulated ion-exchange resin, and a transition metal is added to the polymer-encapsulated ion-exchange resin afterward. The noble metal compounds (e.g., palladium halides, palladium acetate) or complexes (e.g., palladium(II) tetraammine bromide, tetrakis(triphenylphosphine) palladium(0)) diffuse through the polymer layer and deposit on the ion-exchange resin, thus both the ion-exchange resin and the transition metal are encapsulated. Preferably, at least a portion of the noble metal in the resulting catalyst is pre-reduced to the elemental state (e.g., Pd(0)) prior to its use in the process. In yet another example, the noble metal and the ion-exchange resin are encapsulated within a polymer in a single step.

There are many suitable ways to encapsulate a noble metal catalyst within a polymer. Suitable techniques include, for example, spray-drying, spray-chilling, spray-coating, phase separation and coascervation, injection treatment coating, fluid bed coating, dry-on-dry coating, melt extrusion, vapor deposition, in-situ polymerization, including in-situ interfacial polymerization, and the like. These and other microencapsulation techniques are described in the introductory chapter of *Microcapsules and Nanoparticles in Medicine and Pharmacy*, M. Donbrow, Ed., pp. 1-14, and references cited therein, and in G. Beestman, "Microencapsulation of Solid Particles," in *Controlled-Release Delivery Systems for Pesticides* (1999), H. Scher, Ed., pp. 31-54. See also U.S. Pat. No. 6,156,245.

In-situ polymerization is one preferred technique. The noble metal catalyst is suspended in a reaction medium containing monomer(s), an initiator, and other components (e.g., a crosslinking reagent), and polymerization proceeds to give the polymer-encapsulated noble metal catalyst. The monomers can be hydrophilic (e.g., N,N-dimethylacryl-amide), hydrophobic (e.g., styrene), or a combination of these. Suitable techniques include bulk, emulsion, suspension, and interfacial polymerizations. The polymer-encapsulated catalyst can be prepared in such a manner. As an example, styrene or a mixture of styrene and other ethylenic monomer(s) may be polymerized in an aqueous suspension of a noble metal catalyst.

Polymer encapsulation by phase separation/coascervation is another preferred technique. A suitable approach with polystyrene as the polymer encapsulant is illustrated by Kobayashi et al. (see *Chem. Commun.* (2003) 449 and references cited therein; *Angew. Chem., Int. Ed.* 40 (2001) 3469; *J. Am. Chem. Soc.* 120 (1998) 2985). In a particularly convenient coascervation approach taught by Kobayashi for encapsulating a palladium compound, polystyrene is dissolved in warm cyclohexane. Tetrakis(triphenylphosphine)-palladium(0) is dissolved in the mixture. Upon slow cooling to 0° C., phase separation and capsule formation occur. Hexane is added to harden the microcapsules, which are then isolated, washed, and dried. Similarly, a noble metal catalyst is mixed with a solution of a polymer (e.g., polystyrene, polyisobutylene) in a solvent. Upon cooling to a lower temperature or/and the addition of another solvent to reduce the solubility of the polymer in the solvent mixture, phase separation occurs and a polymer-encapsulated noble metal catalyst is obtained.

One interfacial method is illustrated by Ley et al. (see *Chem. Commun.* (2002) 1132 and 1134; and *Chem. Commun.* (2003) 678) in the preparation of polyurea-encapsulated transition metals. In Ley's example, an organic phase containing polymerizable monomers and the transition metal source is dispersed within an aqueous phase that contains emulsifiers and/or stabilizers. Polymerization occurs at the interface to form microcapsule walls. A polyurea-encapsulated noble metal catalyst is analogously prepared by substituting a noble metal catalyst for the transition metal source. For another example of in-situ polymerization to generate microcapsules, see *Adv. Powder Technol.* 13 (2002) 265.

The oxidation catalyst and the noble metal catalyst may be encapsulated within the same polymer. For example, a suspension of an oxidation catalyst in a polymer melt or a solution of a polymer in a solvent may be used to encapsulate the noble metal catalyst by any of the methods described above. The resulting product obtained in such a way comprises a noble metal catalyst and an oxidation catalyst, wherein the oxidation catalyst is encapsulated by the polymer and is primarily distributed within the polymer body surrounding a noble metal catalyst particle.

Polymer-encapsulation of the noble metal catalyst and the oxidation catalyst can improve performance (e.g., rate, selectivity, catalyst life) and filterability and also should reduce the leaching of the noble metal into reaction mixtures.

The polymer-encapsulated noble metal catalyst may be further treated by techniques such as heat treatment, oxidation, reduction, and the like prior to use in the epoxidation process. For example, the catalyst may be reduced under an atmosphere containing hydrogen. The encapsulant polymer and the noble metal may undergo physical or chemical changes as a result of such treatment. For example, an unsaturated polymer (e.g., polybutadiene) may be hydrogenated by hydrogen treatment while the noble metal may be reduced by the same treatment.

The weight ratio of oxidation catalyst:polymer-encapsulated noble metal catalyst is not particularly critical. However, a ratio of 0.01-100 (grams of oxidation catalyst per gram of polymer-encapsulated noble metal catalyst) is preferred.

An olefin is required in the process. Suitable olefins include any olefin having at least one carbon-carbon double bond, and generally from 2 to 60 carbon atoms. Preferably, the olefin is an acyclic alkene of from 2 to 30 carbon atoms. The process of the invention is particularly suitable for epoxidizing $C_2$-$C_6$ olefins. More than one double bond may be present in the olefin molecule, as in a diene or triene. The olefin may be a hydrocarbon, or it may contain functional groups such as halide, carboxyl, hydroxyl, ether, carbonyl, cyano, nitro groups, or the like. The process of the invention is especially useful for converting propylene to propylene oxide.

Oxygen and hydrogen are required. Although any sources of oxygen and hydrogen are suitable, molecular oxygen and molecular hydrogen are preferred. The molar ratio of hydrogen to oxygen can usually be varied in the range of $H_2:O_2$=1:100 to 5:1 and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins.

In addition to the olefin, oxygen, and hydrogen, an inert carrier gas may be used. As the carrier gas, any desired inert gas can be used. Suitable inert gases include helium, argon, nitrogen, and carbon dioxide, and mixtures thereof. Saturated hydrocarbons with 1-8, especially 1-6, and preferably 14 carbon atoms, e.g., methane, ethane, propane, and n-butane, are also suitable. Nitrogen and saturated $C_1$-$C_4$ hydrocarbons are preferred inert carrier gases. Mixtures of the listed inert carrier gases can also be used. The molar ratio of olefin to carrier gas is usually in the range of 100:1 to 1:10 and especially 20:1 to 1:10.

The amount of the oxidation catalyst used may be determined on the basis of the molar ratio of the transition metal contained in the oxidation catalyst to the olefin that is supplied per unit time. Typically, sufficient oxidation catalyst is present to provide a transition metal/olefin per hour molar feed ratio of from 0.0001 to 0.1.

The reaction mixture (excluding the oxidation catalyst and the polymer-encapsulated noble metal catalyst) may be a gas, liquid, supercritical fluid, or a gas/liquid mixture under the reaction conditions. Preferably, at least a portion of the reaction mixture is a liquid under the reaction conditions.

The oxidation catalyst and the polymer-encapsulated noble metal catalyst are preferably in the form of a suspension or fixed-bed. The process may be performed in a continuous flow, semi-batch, or batch mode. It is advantageous to work at a pressure of 1-200 bars. Epoxidation according to the invention is carried out at a temperature effective to achieve the desired olefin epoxidation, preferably at temperatures in the range of 0-200° C., more preferably, 20-150° C.

The process preferably uses a solvent. Suitable solvents are liquid under the reaction conditions. They include, for example, oxygen-containing hydrocarbons such as alcohols, aromatic and aliphatic solvents such as toluene and hexane, chlorinated aromatic and aliphatic solvents such as chlorobenzene and methylene chloride, nitrites such as acetonitrile, carbon dioxide, and water, and mixtures thereof. Suitable oxygenated solvents include alcohols, ethers, esters, ketones, carbon dioxide, water, and the like, and mixtures thereof. Preferred oxygenated solvents include water and lower aliphatic $C_1$-$C_4$ alcohols such as methanol, ethanol, isopropanol, and tert-butanol, and mixtures thereof. Fluorinated alcohols can be used.

It may be advantageous to use a buffer. The buffer is employed in the reaction to inhibit the formation of glycols or glycol ethers during epoxidation, and it can improve the reaction rate and selectivities. The buffer is typically added to the solvent to form a buffer solution, or the solvent and the buffer are added separately. Useful buffers include any suitable salts of oxyacids, the nature and proportions of which in the mixture are such that the pH of their solutions preferably ranges from 3 to 12, more preferably from 4 to 10, and most preferably from 5 to 9. Suitable salts of oxyacids contain an anion and a cation. The anion may include phosphate, carbonate, bicarbonate, sulfate, carboxylates (e.g., acetate), borate, hydroxide, silicate, aluminosilicate, or the like. The cation may include ammonium, alkylammonium (e.g., tetraalkylammoniums, pyridiniums), alkylphosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of the buffer in the solvent is from 0.0001 M to 1 M, preferably from 0.0005 M to 0.3 M. The buffer may include ammonium hydroxide which can be formed by adding ammonia gas to the reaction system. For instance, one may use a pH=12-14 solution of ammonium hydroxide to balance the pH of the reaction system. More preferred buffers include alkali metal phosphates, ammonium phosphate, and ammonium hydroxide.

Following examples merely illustrate the invention. Those skilled in the art will recognize many variations that are within the spirit of the invention and scope of the claims.

COMPARATIVE EXAMPLE 1

Pd/A36 Catalyst

Amberlyst 36 resin (A36, an acidic resin obtained from Rohm & Haas) (50.5 g) is washed with methanol (100 g) in a beaker under gentle agitation. The methanol is then decanted. The methanol washing step is repeated six times. To a suspension containing the above washed A-36 and 100 g of methanol, a solution made of 1.71 g of palladium acetate and 70 g of acetone is added with mixing at room temperature. After 30 min, the solid is filtered and washed with 100 g of methanol, then dried in a vacuum oven at 60° C. to constant weight. The dried solid (Catalyst A) (46.5 g) contains 1.9 wt. % Pd.

EXAMPLE 2

Polystyrene-Encapsulated Pd/A36 Catalyst

Into a 2-oz crown cap bottle containing a solution of 13 g of styrene and 0.15 g of 2,2'-azobis(isobutyronitrile) (AIBN), a solution of 0.15% poly(vinyl alcohol) in water (120 g), and 30 g of Catalyst A from Example 1 are charged. After the bottle is purged with nitrogen to eliminate oxygen, the bottle is capped and the suspension polymerization effected by end-over-end agitation of the bottle in a heated oil bath at 70° C. for 3 h, followed by another 3 h at 90° C. After being cooled to room temperature, the polymer-encapsulated catalyst is filtered, washed twice with deionized water, and dried in a vacuum oven at 60° C. to constant weight. The product (Pd/A36/PS, Catalyst B) contains 1.0 wt. % Pd.

COMPARATIVE EXAMPLE 3

Epoxidation of Propylene with Pd/A36 Catalyst

An ammonium phosphate buffer solution (0.1 M, pH 6) is prepared as follows. Ammonium dihydrogen phosphate (11.5 g) is dissolved in 900 g of de-ionized water. Aqueous ammonium hydroxide (30 wt. % $NH_4OH$) is added to the solution until the pH reads 6 via a pH meter. The volume of the solution is then increased to exactly 1000 mL with additional deionized water.

Titanium silicalite-1 (TS-1) samples are prepared by following procedures disclosed in U.S. Pat. Nos. 4,410,501 and 4,833,260.

A 300-mL stainless steel reactor is charged with 0.10 g of Catalyst A, 0.60 g of TS-1 powder (1.9 wt. % Ti, calcined at 550° C. in air), 13 g of buffer solution as prepared above, and 100 g of methanol. The reactor is then charged to 300 psig with a feed gas consisting of 2 volume percent (vol. %) hydrogen, 4 vol. % oxygen, 5 vol. % propylene, 0.5 vol. % methane, and the balance nitrogen. The pressure in the reactor is maintained at 300 psig via a back pressure regulator with the feed gases passed continuously through the reactor at 1600 mL/min (measured at 23° C. and 1 atmosphere pressure). In order to maintain a constant solvent level in the reactor during the run, the oxygen, nitrogen and propylene feeds are passed through a 2-L stainless steel vessel (saturator) preceding the reactor containing 1.5 L of methanol. The reactor is stirred at 1500 rpm. The reaction mixture is heated to 60° C. and the gaseous effluent is analyzed by an online gas chromatograph (GC) every hour and the liquid analyzed by offline GC at the end of the 18 h run. The products formed include propylene oxide (PO), propane, and derivatives of propylene oxide such as propylene glycol, propylene glycol monomethyl ethers, dipropylene glycol, and dipropylene glycol methyl ethers. The results are shown in Table 1. The catalyst productivity is defined as the grams of PO formed (including PO subsequently reacted to form PO derivatives) per gram of catalysts (TS-1 and Pd/A36 catalyst) per hour. POE (mole)=moles of PO+moles of PO units in the PO derivatives. PO/POE=(moles of PO)/(moles of POE)×100. Propylene to POE selectivity=(moles of POE)/(moles of propane formed+moles of POE)×100.

EXAMPLE 4

Epoxidation of Propylene with Polystyrene-Encapsulated Pd/A36 Catalyst

The procedure of Example 3 is repeated except 0.20 g of Catalyst B is used instead of 0.10 g of Catalyst A. Results are shown in Table 1.

The reaction mixtures in Comparative Example 3 and Example 4 contain approximately the same amounts of Pd and TS-1. As Table 1 shows, higher epoxide productivity is obtained with the polystyrene-encapsulated Pd/A-36 catalyst.

TABLE 1

Epoxidation of Propylene

| | Example | |
|---|---|---|
| | C3 | 4 |
| Pd Catalyst | Catalyst A | Catalyst B |
| Pd, wt. % | 1.9 | 1.0 |
| Pd Catalyst, g | 0.10 | 0.20 |
| Catalyst Productivity, g POE/g cat/h | 0.28 | 0.37 |
| PO/POE, % (mole/mole) | 91 | 84 |
| Propylene to POE Selectivity, % (mole/mole) | 91 | 86 |

We claim:

1. An epoxidation process comprising reacting an olefin, hydrogen, and oxygen in the presence of an oxidation catalyst comprising a transition metal zeolite, and a polymer-encapsulated noble metal catalyst comprising a noble metal and an ion-exchange resin.

2. The process of claim 1 wherein the transition metal zeolite is a titanium zeolite.

3. The process of claim 1 wherein the transition metal zeolite is TS-1.

4. The process of claim 1 wherein the noble metal is selected from the group consisting of palladium, platinum, gold, rhenium, silver, and mixtures thereof.

5. The process of claim 1 wherein the ion-exchange resin has a capacity of from 1 to 10 eq/kg.

6. The process of claim 1 wherein the ion-exchange resin is an acidic ion-exchange resin.

7. The process of claim 1 wherein the ion-exchange resin is a sulfonic acid polystyrene resin.

8. The process of claim 1 wherein the polymer is selected from the group consisting of polystyrenics, polyolefins, and mixtures thereof.

9. The process of claim 1 wherein the polymer is polystyrene.

10. The process of claim 1 wherein the oxidation catalyst is encapsulated within a polymer.

11. The process of claim 1 wherein the oxidation catalyst is encapsulated within the same polymer.

12. The process of claim 1 wherein the ion-exchange resin comprises a cation selected from the group consisting of alkali metal and alkaline earth metal ions, and mixtures thereof.

13. The process of claim 1 wherein the noble metal catalyst further comprises a component selected from the group consisting of titania, zirconia, niobia, silica, alumina, silica-alumina, titania-silica, zirconia-silica, niobia-silica, and mixtures thereof.

14. The process of claim 1 wherein the reaction is performed in the presence of a solvent.

15. The process of claim 14 wherein the solvent is selected from the group consisting of alcohols, ethers, esters, ketones, carbon dioxide, water, and mixtures thereof.

16. The process of claim 14 wherein the reaction is performed in the presence of a buffer.

17. The process of claim 16 wherein the buffer comprises an anion selected from the group consisting of phosphate, carbonate, sulfate, hydroxide, acetate, and the mixtures thereof; and a cation selected from the group consisting of ammonium, alkylammonium, alkylphosphonium, alkali metal, and alkaline earth metal ions, and the mixtures thereof.

18. The process of claim 1 wherein the olefin is one or more $C_2$-$C_6$ olefins.

19. The process of claim 1 wherein the olefin is propylene.

20. An epoxidation process comprising reacting propylene, hydrogen, and oxygen in a solvent in the presence of a buffer, an oxidation catalyst comprising a titanium zeolite, and a polymer-encapsulated noble metal catalyst comprising a noble metal and a sulfonic acid polystyrene resin.

* * * * *